United States Patent [19]

Veit et al.

[11] 4,272,647
[45] Jun. 9, 1981

[54] SPEECH AID APPARATUS

[76] Inventors: Ivar Veit, Auf dem Schild 6, 2400 Lübeck; Liesbet Sickel, Dr. Ringen Str. 49, 5063 Overath; Konstantin Gatzsch, Hinter den Wiesen 15, 5 Köln 91, all of Fed. Rep. of Germany

[21] Appl. No.: 33,290

[22] Filed: Apr. 25, 1979

[30] Foreign Application Priority Data

Apr. 26, 1978 [DE] Fed. Rep. of Germany ....... 2818144

[51] Int. Cl.³ .............................................. A61F 1/20
[52] U.S. Cl. ................................................. 179/1 AL
[58] Field of Search ......... 179/1 AL, 121 C, 115.5 R, 179/115.5 PC, 119; 3/1.3

[56] References Cited

U.S. PATENT DOCUMENTS 4,028,492  6/1977  Sickel .............................. 179/1 AL Primary Examiner—Daryl W. Cook
Assistant Examiner—Joseph A. Popek
Attorney, Agent, or Firm—Sprung, Felfe, Horn, Lynch & Kramer

[57] ABSTRACT

A speech aid apparatus for laryngectomees includes a first housing having disposed therein, a sound head with a hard diaphragm held therein, an electrodynamic oscillator connected to the sound head and including a magnet system with an oscillator coil, a plunger connected thereto and a soft diaphragm vibrationally connected to the first housing through the plunger whereby the soft diaphragm sets the hard diaphragm into vibration. The apparatus also includes a second housing for a power supply and an operating switch and the two housings are releasably mechanically and electrically connected by a bayonet joint. The magnet system includes a pot type magnetic arrangement with an axially polarized very thin annular permanent magnet held between two pole rings made of a soft magnetic material and having rotational symmetry. The upper pole ring is pot shaped with a downwardly open annular gap concentric with the central opening of the magnet arrangement and the oscillator coil projects into the annular gap. The plunger is connected to the oscillator coil and extends freely through the central opening of the magnet arrangement.

8 Claims, 4 Drawing Figures

SPEECH AID APPARATUS

BACKGROUND OF THE INVENTION

The invention relates to a speech-aid apparatus for laryngectomees which comprises a sound head with a hard diaphragm held therein, an electrodynamic oscillator connected to the sound head and consisting of a magnet system with an oscillator coil and, connected thereto, a plunger which through a soft diaphragm is suspended from the housing of the oscillator and is adapted to set the hard diaphragm into vibration, and a generator section which comprises the power supply and an operating switch and is connectable mechanically and electrically, through a bayonet joint or the like, to the oscillator.

A speech-aid apparatus of this type is described and shown in U.S. Pat. No. 4,028,492 and serves as a substitute for the missing vocal cords of the laryngectomee. When the apparatus is held against the throat, sound is generated in the cavity of the mouth and pharynx which by the usual speaking movements may be shaped into readily comprehensible speech. In the process, the plunger is set into vibration by the electrodynamic oscillator and transfers these vibrations as mechanical pulses to the hard diaphragm which is in direct contact with the throat. Using for the magnet system a permanent magnet made of a hard magnetic material of the class of $SECo_5$ magnets permits the oscillator to be made very small and yet to be very efficient. This makes it possible to use the oscillator with the sound head threaded onto it separately from the generator section and to fasten it in a holder to the throat of the user, who is then able to speak unhindered, with both hands free for activities other than holding the speech-aid apparatus.

SUMMARY OF THE INVENTION

The object of the invention is to improve the type of speech-aid apparatus described above in such a way that the overall length of the oscillator is reduced still further so that the oscillator with its sound head carried at the throat of the user is still less conspicuous and bothersome.

In accordance with the invention, this object is accomplished in that the magnet system consists of a pot-type magnet arrangement comprising an axially polarized and very thin annular permanent magnet which is held between two pole rings of a soft magnetic material and having rotational symmetry, the upper one of these pole rings being pot-shaped, so that the annular gap of the pot-type magnet arrangement is open downwardly and the oscillator coil projects into it, and that the plunger connected to the oscillator coil extends freely through the central opening of the pot-type magnet arrangement.

This solution in accordance with the invention offers the advantage that as a result of the inverse arrangement of the pot-type magnets, that is to say, of the downwardly open annular air gap, and despite smaller dimensions, the travel of the oscillator coil is not limited in the downward direction and is limited in the upward direction only by the abutting of the plunger. The width of this annular air gap should be between 0.6 and 1.3 mm.

As a further refinement of the invention, the generator section and the unit consisting of sound head and oscillator are adapted to be electrically interconnected by means of a flexible cable having at both ends a bayonet-type fitting adapted to be connected to the oscillator and to the generator section, respectively.

This makes it possible to connect the unit consisting of sound head and oscillator easily and quickly to the generator section even over a fairly large distance. The cable with its two bayonet-type fittings can readily be replaced as a unit when damaged, and since normally it is not connected to the generator section, it is not subject to excessive wear and tear.

In accordance with a further characteristic of the invention, the unit consisting of sound head and oscillator with a bayonet-type fitting thereon is adapted to be accommodated in a can-like holder to be fastened to the throat of the user by means of a tape. The can-type holder advantageously has an actuating opening at two opposed points for adjustment of the sound head.

In accordance with still another characteristic of the invention, the generator section is provided with two spring clips to hold a belt whereby the generator section may be fastened to the body of the user.

Further characteristics and advantages of the invention will become apparent from the description which follows of an embodiment shown in the drawing, wherein:

DETAILED DESCRIPTION OF THE INVENTION

Figure 2:
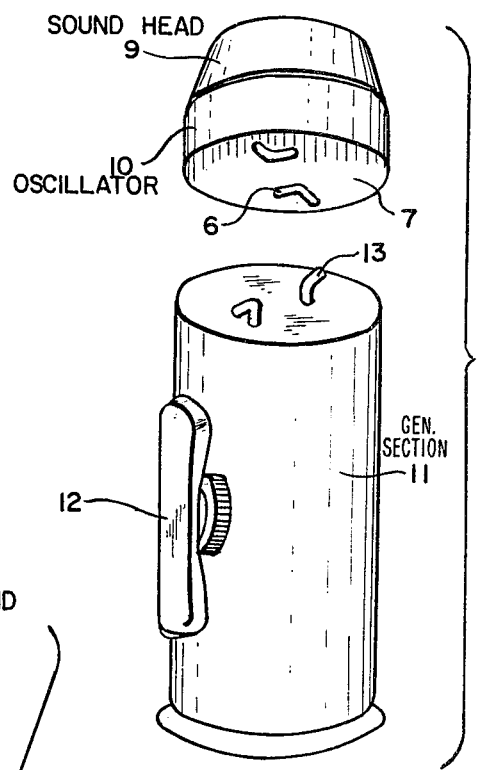
FIG. 2 is a perspective view of the speech-aid apparatus with the oscillator and sound head removed.

As may be seen from FIG. 2, the speech-aid apparatus in accordance with the invention comprises a generator section 11 consisting essentially of an electronic pulse generator with adjusting potentiometers for adjustment of the pulse repetition frequency and the magnitude of the current pulses as desired by the user of the apparatus. Also provided on the generator section 11 is an on/off switch 12 for placing the speech-aid apparatus in operation. The on/off switch 12 preferably has an enlarged pushbutton permitting it to be operated securely also through clothing by means of the upper arm or forearm, for example.

Through a double bayonet joint 13, the generator section 11 can be connected both electrically and mechanically to the oscillator 10, which is provided with cutouts 6 which are engaged by the prongs of the bayonet joint 13. The oscillator 10 is threaded onto a sound head 9. This unit consisting of sound head 9 and oscillator 10 is shown in greater detail in FIG. 1.

The oscillator 10 essentially consists of an axially polarized, very thin permanent magnet 1 fabricated from a compound of cobalt and rare-earth elements (samarium), for example, a type VACOMAX 145 or 155 SECo magnet manufactured by Vakuumschmelze Hanau. This permanet magnet 1 is mounted between two pole rings 2 made of a soft magnetic material and having rotational symmetry. The upper pole ring 2 is pot-shaped and downwardly open so that a pot-type magnet arrangement with downwardly open annular gap is formed which is threaded into the housing 18 of the oscillator 10. An oscillator coil 3 projects from below into the annular gap of the pot-type magnet arrangement, said coil being electrically connected, when mechanically connected to the bayonet-joint cutout 6 in the bottom 7 of the housing of the oscillator 10, through two stranded conductors 19. A plunger 4 which through a plate 20 is rigidly joined to the oscillator coil 3 extends centrally through a tubular rivet 8 which holds the pot-type magnet arrangement together. The projecting portion of the plunger 4 is fixed to a soft diaphragm 5 which is fastened to the upper pole ring 2.

The sound head 9 is joined to the upper pole ring 2, and hence to the oscillator 10, through a threaded joint 21. The upper portion of the sound head 9 has a recess into which a hard diaphragm 22 is set which must be pressed against the throat of the user. The hard diaphragm 22 is mounted in the sound head 9 by means of a threaded tensioning disk 24. In the center of the hard diaphragm 22 there is an abutment 25 against which the plunger 4 suspended from the soft diaphragm 5 is thrust by the effect of the electromagnetic field produced when current flows through the oscillator coil 3.

The spacing of the upper end of the plunger 4 from the abutment 25 in the rest position may be varied by rotating the sound head 9 relative to the oscillator 10. Said spacing should be comprised between 1 and 5 mm.

Figure 1:
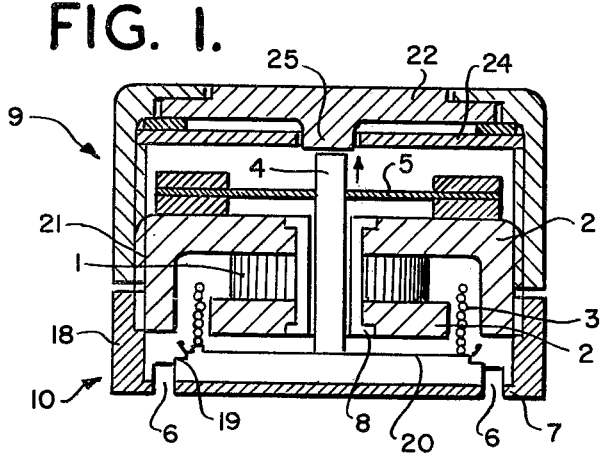
FIG. 1 is a longitudinal section through a unit, consisting of sound head and oscillator, of a speech-aid apparatus constructed in accordance with the invention.

The inverted pot-type magnet arrangement in accordance with the invention, shown in FIG. 1, offers two advantages: In the first place, in contrast to the arrangement according to U.S. Pat. No. 4,028,492 the travel of the oscillator coil 3 is not limited in the downward direction and is limited in the upward direction only by the desired abutting of the plunger 4 on the hard diaphragm 22. Secondly, the stranded conductors 19 connecting the oscillator coil 3 to the bayonet-joint elements 13 are loosely disposed in space and therefore do not brush or rub against nearby parts of the apparatus or are otherwise subject to wear and tear.

The oscillator 10 and its sound head 9, and hence the entire speech-aid apparatus, may be optimized with regard to the force producible by the oscillator. Since the force generated by an electromagnetic system is a function of air-gap induction (magnetic material and geometry of assembled system), length of the conductor (number of turns of coil), and magnitude of the current flowing through the coil, the influences of some of the individual parameters will be in mutual opposition. For example, while increasing the number of turns of the coil will increase the producible force, it may reduce the producible current, and hence the force. Tests have shown that the force may be increased both by reducing the air gap and by increasing the magnetic field strength. A further increase in force can readily be secured through an appropriate change in coil characteristics. It has been found that optimization is possible within the following boundary values:

Diameter of oscillator coil with external annular magnet, between 8 and 12 mm, and with internal annular magnet, between 18 and 24 mm; number of turns of oscillator coil, 50 to 200; diameter of wire used in coil, 0.1 to 0.15 mm.

Figure 3:
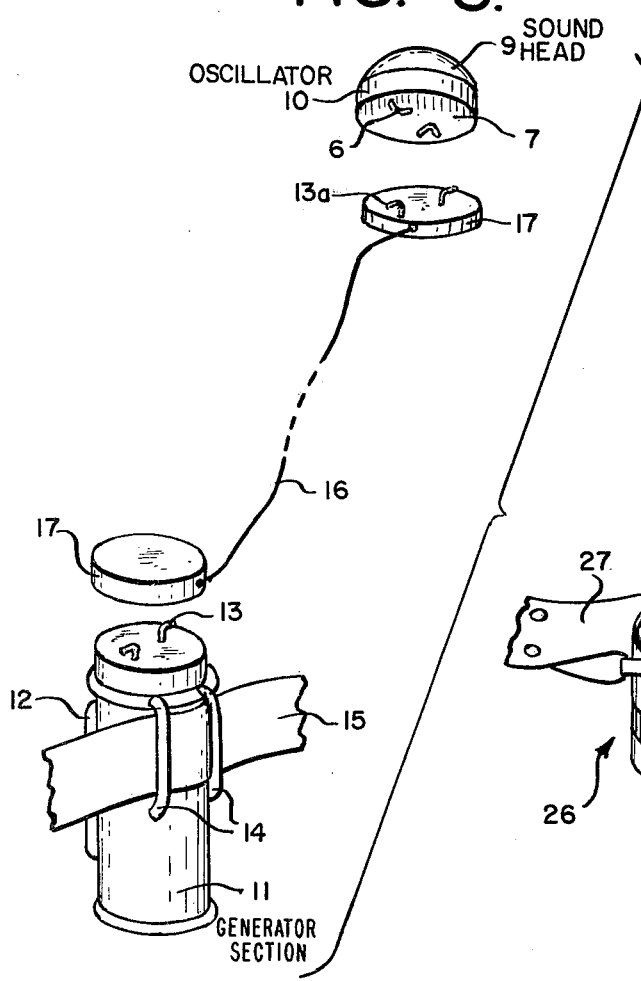
FIG. 3 is a view of the speech-aid apparatus and, spaced therefrom, of the oscillator with sound head connected to the generator section by means of a cable.

As shown in FIG. 3, the generator section 11 may be provided with two spring clips 14 through which a belt 15 is looped whereby the generator section 11 may be fastened to the body of the user.

FIG. 3 further shows a mode of connecting the speech-aid apparatus in which the unit consisting of sound head 9 and oscillator 10 is physically separated from the generator section 11. For the electrical connection, a flexible cable 16 is provided each of whose two ends carries a bayonet-joint element 17, one of these having cutouts (not shown) which may be coupled to the bayonet-joint elements 13 of the generator section 11 while the other has pinlike bayonet-joint elements 13a which have the same form as the bayonet-joint elements 13 of the generator section and engage appropriate cutouts 6 in the bottom 7 of the housing of the oscillator 10. In this way, the oscillator section 11 is electrically connected to the oscillator 10 and its sound head 9.

Figure 4:
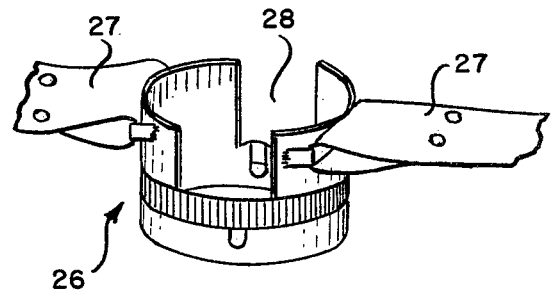
FIG. 4 is a perspective view of a can-type holder for the oscillator with sound head.

When the speech-aid apparatus is used in the manner illustrated in FIG. 3, the unit consisting of sound head 9 and oscillator 10 is accommodated at the throat of the user in a can-type holder 26 shown in FIG. 4. This holder may be fastened to the throat of the user by means of a tape such as a hook-and-loop strap 27 and is provided at two opposite points with an actuating opening 28 through which the spacing of the hard diaphragm 22 of the sound head 9 from the plunger 4 may be adjusted.

We claim:

1. A speech-aid apparatus for laryngectomees, comprising: a first housing having disposed therein a sound head with a hard diaphragm held therein, an electrodynamic oscillator connected to the sound head and including a magnet system with an oscillator coil, a plunger, connected thereto and a soft diaphragm vibrationally connected to the first housing through the plunger, whereby the soft diaphragm sets the hard diaphragm into vibration; and a second housing for a power supply and an operating switch and means for releasably mechanically and electrically connecting the two housings comprising a bayonet joint wherein the magnet system comprises a pot-type magnet arrangement having a central opening and comprising an axially polarized, very thin annular permanent magnet held between two pole rings made of a soft magnetic material and having rotational symmetry, the upper one of the two rings being pot-shaped, with a downwardly open annular gap concentric with the central opening and the oscillator coil projecting into it, and wherein the plunger is connected to the oscillator coil and extends freely through the central opening of the pot-type magnet arrangement.

2. A speech-aid apparatus according to claim 1, wherein the releasable connecting means comprises a flexible cable having a bayonet-joint element at both ends, one of which may be secured to the first housing, the other to the second housing.

3. A speech-aid apparatus according to claim 2, further comprising a can-like holder receptive of the first housing and means for securing same to the throat of the user comprising a strap.

4. A speech-aid apparatus according to claim 3, wherein the can-like holder is provided with an actuating opening at two opposite points for adjustment of the sound head.

5. A speech-aid apparatus according to claim 1, wherein the second housing is provided with two spring clips for holding a belt whereby the second housing may be carried on the body of the user.

6. A speech-aid apparatus according to claim 1, wherein the spacing between the plunger in the rest position and the hard diaphragm ranges from 1 to 5 mm.

7. A speech-aid apparatus according to claim 1, wherein the width of the annular gap of the magnet system ranges from 0.6 to 1.3 mm.

8. A speech-aid apparatus according to claim 1, wherein the oscillator coil has from 50 to 200 turns of wire between 0.1 and 0.15 mm thick, and a diameter ranging from 8 to 12 mm for the lower pole ring and from 18 to 24 mm for the upper pole ring.

* * * * *